(12) United States Patent
Philippon (10) Patent No.: US 6,440,141 B1
(45) Date of Patent: Aug. 27, 2002

(54) METHOD AND APPARATUS FOR TREATING OSTEOCHONDRAL PATHOLOGIES

(75) Inventor: Marc J. Philippon, Boca Raton, FL (US)

(73) Assignee: Oratec Interventions, Inc., Menlo Park, CA (US)

( * ) Notice: Subject to any disclaimer, the term of this patent is extended or adjusted under 35 U.S.C. 154(b) by 0 days.

(21) Appl. No.: 09/624,689

(22) Filed: Jul. 24, 2000

(51) Int. Cl.⁷ .............................................. A61B 17/58
(52) U.S. Cl. .............................. 606/99; 604/60; 604/62
(58) Field of Search ................................ 600/562–568; 606/79–105; 604/59–64

(56) References Cited

U.S. PATENT DOCUMENTS

| | | | |
|---|---|---|---|
| 4,474,572 A | * 10/1984 | McNaughton et al. | 604/61 |
| 4,994,028 A | * 2/1991 | Leonard et al. | 604/59 |
| 5,713,374 A | 2/1998 | Pachence et al. | 128/898 |
| 5,842,477 A | 12/1998 | Naughton et al. | 128/898 |
| 5,855,608 A | 1/1999 | Brekke et al. | 623/11 |
| 5,981,825 A | 11/1999 | Brekke | 623/11 |
| 6,001,352 A | 12/1999 | Boyan et al. | 424/93.7 |
| 6,005,161 A | 12/1999 | Brekke et al. | 623/16 |
| 6,270,503 B1 | * 8/2001 | Schmieding | 606/88 |
| 6,287,313 B1 | * 9/2001 | Sasso | 606/96 |

OTHER PUBLICATIONS

Weisl, H.; "Pathological Features of Osteoarthritis" Textbook of Orthopedics, vol. 62–B (1) 1980, pp. 37–42.

* cited by examiner

Primary Examiner—Corrine McDermott
Assistant Examiner—Urmi Chattopadhyay
(74) Attorney, Agent, or Firm—Fish & Richardson P.C.

(57) ABSTRACT

Systems and methods are described for treating osteochondral pathologies. An implantable prosthesis for treating osteochondral pathologies includes: a porous substrate; and a substance positioned within the porous substrate that is elutable with regard to the porous substrate. The systems and methods provide advantages because a baited route is provided to attract mesenchymal stem cells from the cancellous bone underlying the articular surfaces up to chondral lesions within the joint, thereby promoting the growth of chondrocytes in the area of the chondral lesions.

5 Claims, 5 Drawing Sheets

METHOD AND APPARATUS FOR TREATING OSTEOCHONDRAL PATHOLOGIES

BACKGROUND OF THE INVENTION

1. Field of the Invention

The invention relates generally to the field of treating osteochondral pathologies. More particularly, the invention relates to methods and apparatus for implanting a substance eluting porous substrate into a bony defect to promote repair of osteochondral lesions.

2. Discussion of the Related Art

Interventions for the treatment of chondromalacia and osteoarthritis include a variety of modalities, which include arthroscopic debriedment, microfracture techniques, intraarticular injection of medicaments, osteochondral transplants, and open surgical interventions such as chondrocyte transplantation via cell culturing techniques. None of these techniques has achieved the goal of offering a technically and economically feasible technique for promoting the growth of hyaline cartilage cells within osteochondral lesions.

Cartilaginous tissues covering the articulating ends of bones are composed of collagen, primarily Type II collagen and chondrocytes. These tissues are addressed surgically for indications such as chondral lesions of traumatic origin, and degeneration of the articular surfaces as in osteoarthritis.

Osteoarthritis is a degenerative condition of the articular surfaces of the joints often in areas where weight bearing or load bearing surfaces have lost their fluid retaining capacity. The fluid retaining capacity is provided by the proteoglycan component of the cartilage matrix that normally opposes the forces exerted on the ends of articulating bones. It is the biochemical capability of fluid that provides a cushion between these surfaces.

Chondromalacia is a condition of the articular cartilage, particularly the knee that describes the degeneration of the articular surfaces as seen in osteoarthritis. This descriptor indicates a fraying or fibrillation of the articular cartilaginous tissues. Chondromalacia proceeds from this fibrillated state to a complete denuding of the articular tissues leaving only the bony surface, which eventually erodes. This erosion proceeds into the bony structures.

Debriedment refers to the mechanical removal of compromised tissues using cutting and scraping instruments. In the early stages, chondromalacia can be treated by mechanical cutting of the frayed tissue by a bladed hand instrument or by high speed mechanical shavers in common use in arthroscopic surgery today. The condition can also be treated using thermal and laser techniques. None of these treatments reverses or stops the degenerative process. These treatments do nothing to repair tissues. These treatments seek to improve function or reduce pain by removing tissues that interfere with function of the joint.

Electrothermal and lasers approaches have been utilized to perform a thermal chondroplasty whereby the fibrillated cartilage surface is treated with heat to coagulate the fibrillated or non-intact cartilage tissue, thus sealing the articular cartilage surface, and thereby inhibiting further degradation of the cartilage matrix. The mechanical aspects of the knee joint are thus maintained with little change in articular function. The use of the laser for treatment of chondromalacia has focused on the ablative (cutting and removing) effects of the laser rather than the low temperature coagulative sealing effects of electrothermal energies.

Microfracture techniques are employed when the cartilage is completely gone from an area of the articular surface. This approach attempts to create a channel from the cancellous bone underlying the articular surfaces to the joint space in hopes that this access to the cancellous bone will provide an avenue for mesenchymal stem cells which are produced in the bone to migrate to the chondral lesions within the joint, thereby promoting the growth of chondrocytes in the area of the defect. This technique is still considered controversial despite its relatively widespread use because of the lack of definitive clinical data.

Osteochondral transplants attempt to replace the articular surface by using 'plugs' harvested from healthy non-weight bearing surfaces, and implanting them into recipient sites prepared in the target lesion. This technique is less than satisfying in that normal healthy tissues must be sacrificed to be placed in the defect which may result in a failure of the transplant leaving both donor/harvest site and target lesion with a significant bony insult.

Cell culturing techniques have been evaluated for several years with some success in terms of ameliorating patient's symptoms. The primary technique consists of two procedures, the first of which is done to collect a patient's chondrocytes as a biopsy sample. These "cells" are then sent to a company that "cultures" the cells and "grows" them so that there is enough tissue to re-implant in the patient's chondral lesion. In a second procedure the cultured cells are re-implanted into the chondral defect and a periosteal flap is utilized to contain the cells within the defect. The tissue that is seen some time after autologous transplantation is characterized as "hyaline like" since the tissue contains chondrocytes but cannot be characterized as hyaline cartilage. Clinical results at a small number of centers show some benefits but the cost and difficulty associated with a "two surgery" procedure leave much room for improvement in the treatment of this condition. New efforts at simplifying this procedure and reducing costs are underway but is unclear whether any of these will be any more successful in promoting hyaline cartilage growth.

For these reasons, it would be desirable to provide a method and apparatus for promoting chondrocyte growth that most closely replicates the normal articular cartilage with a procedure that is less expensive, less invasive and more efficacious.

SUMMARY OF THE INVENTION

A goal of the invention is to satisfy the above-discussed requirements of keeping costs and invasiveness low while simultaneously replicating the normal articular cartilage and achieving high effectiveness which, in the case of the prior art, are not simultaneously satisfied.

One embodiment of the invention is based on an implantable prosthesis for treating osteochondral pathologies, comprising: a porous substrate; and a substance positioned within said porous substrate that is elutable with regard to said porous substrate. Another embodiment of the invention is based on a surgical instrument, comprising a trocar having a proximal end and a distal end; a drill locatable within said trocar to prepare a subchondral bleeding bed for insertion of an implantable prosthesis, said drill having i) a flexible shaft that is extendable beyond said proximal end of said trocar and ii) a rigid tip that is simultaneously extendable beyond said distal end of said trocar, said rigid tip adapted to cut a recess into said subchondral bleeding bed for insertion of an implantable prosthesis; and an advancement mechanism adapted to apply pressure to said implantable prosthesis. Another embodiment of the invention is based on a method for treating osteochondral pathologies, comprising a method for treating osteochondral pathologies, comprising: positioning a distal end of a surgical instrument at a site targeted for subchondral implantation of an implantable prosthesis that carries an elutable substance; cutting a recess into a subchondral bleeding bed for insertion of said implantable prosthesis; and press-fitting said implantable prosthesis into said recess at said site and permitting said elutable substance to interact with said subchondral bleeding bed. Another embodiment of the invention is based on a method of making an implantable prosthesis for treating osteochondral pathologies, comprising: forming a cavity in a porous substrate; introducing a substance, which is elutable with regard to said porous substrate, into said cavity; and coupling a cap to said porous substrate to enclose said substance within said cavity.

These, and other goals and embodiments of the invention will be better appreciated and understood when considered in conjunction with the following description and the accompanying drawings. It should be understood, however, that the following description, while indicating preferred embodiments of the invention and numerous specific details thereof, is given by way of illustration and not of limitation. Many changes and modifications may be made within the scope of the invention without departing from the spirit thereof, and the invention includes all such modifications.

BRIEF DESCRIPTION OF THE DRAWINGS

A clear conception of the advantages and features constituting the invention, and of the components and operation of model systems provided with the invention, will become more readily apparent by referring to the exemplary, and therefore nonlimiting, embodiments illustrated in the drawings accompanying and forming a part of this specification, wherein like reference characters (if they occur in more than one view) designate the same parts. It should be noted that the features illustrated in the drawings are not necessarily drawn to scale.

DESCRIPTION OF PREFERRED EMBODIMENTS

The invention and the various features and advantageous details thereof are explained more fully with reference to the nonlimiting embodiments that are illustrated in the accompanying drawings and detailed in the following description of preferred embodiments. Descriptions of well-known components and processing techniques are omitted so as not to unnecessarily obscure the invention in detail.

The below-referenced U.S. Patents disclose embodiments that were satisfactory for the purposes for which they were intended. The entire contents of U.S. Pat. Nos. 5,713,374; 5,842,477; 5,855,608; 5,981,825; 6,001,352; and 6,005,161 are hereby expressly incorporated by reference into the present application as if fully set forth herein.

Overview

The invention can include preparing a recess into a sub-chondral bone. The recess functions as a receptacle. The recess can be prepared with a twist drill. Alternatively, the recess can be prepared by cutting and removing a core with a plug drill.

The invention can include implanting (e.g., inserting or depositing) an implantable prosthesis (e.g., medicament carrier or vehicle) into sub-chondral bone. If the prosthesis is implanted into sub-chondral bone, it can be termed an osteochondral plug. The implantable prosthesis can be implanted into a recess (e.g., such as the recess described above). The recess can be previously prepared at a predetermined site of the sub-chondral bone. Alternatively, the recess can be prepared just before the prosthesis is implanted.

A plurality of the prostheses can be implanted across a surface in need thereof The plurality of prostheses can be deployed in a pattern, randomly, and/or where they are most likely to be effective, as determined by the physician.

The invention can include heat treating the surface that results from implanting the prosthesis. The heat treatment can smooth and/or consolidate the resulting surface. The heat treatment can effected with one or more ohmic heater (s), electrode(s) (e.g., radio frequency), laser(s), and/or ultrasonic transducer(s).

Implantable Prosthesis

The invention can include an implantable prosthesis. The implantable prosthesis functions to supplement and encourage healing of load bearing cartilage surfaces.

The implantable prosthesis can include a substrate. The substrate can be formed from a synthetic material or natural bone obtained from the same, or another, site. The use of a synthetic material provides a significant advantage. By using a synthetic material, the invention provides a significant advantage compared to traditional techniques since the need to obtain a natural bone plug from another site is obviated. Consequently, the number of sites that are traumatized is reduced by 50% compared to the situation where natural bone substrates are obtained from another site.

The substrate can include a porous material. Preferred embodiments of the invention include a continuous porous phase, thereby permitting easy passage through the substrate and extended intergrowth of cells. The porous substrate can include a semi-permeable material. In preferred embodiments, the substrate is made of a synthetic porous biocompatible material, such as, for example bioglass.

The substrate can include a cavity that defines a void into which a substance can be placed. The cavity can be machined into, or formed in, the substrate. In preferred embodiments, the substance is elutable through and/or from the substrate.

The substance can contain a chondrocyte inductive medicament. By implanting a substrate into the previously prepared recess, the medicament can be delivered directly into the sub-chondral bone for the purpose of allowing the slow elution of the medicament into an articular lesion. The use of a chondrocyte inductive medicament provides a significant advantage. This technique provides a conduit for stem cells to travel from their site of origin in the cancellous bone compartment into the joint capsule via the tunnel created by the placement of the carrier and the porous nature of the carrier.

The medicament can include piascladine. The medicament can be a formulation of any substance or combination of substances that might be beneficial to promoting joint physiology and tissue repair. The medicament can include 50 mg avocado, 150 mg soya, 100 mg inert and 50 mg growth hormone.

The medicament can be formed into a solid pellet. The pellets can be cannulated to accept a shape memory wire during insertion. Alternatively, the pellets can be relieved on one side and an end to accept a shape memory sleeve. In ether event, upon reversion of the shape memory element, the pellet will be deformed against the interior wall of the substrate that defines the cavity. In turn, the exterior wall of the substrate will be deformed, thereby exerting stress against the recess to help hold the substrate in place.

Figure 1:
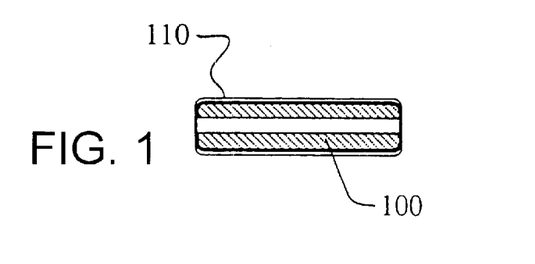
FIG. 1 illustrates a schematic side view of a pellet, representing an embodiment of the invention.

Referring to FIG. 1, a pellet 100 is depicted. The pellet 100 can be formed of the elutable substance. The pellet 100 includes a shape memory material sleeve 110. Alternatively, the pellet 100 can be cannulated and include a shape memory material wire. After implementation, these shape memory materials can be deflected due to the patient's body heat, thereby generating stress to help hold the implantable prosthesis in place.

A cap can be coupled to the substrate to seal the cavity and/or enclose the substance within the cavity. The cap can include a layer that is formed from an artificial material or natural cartilage obtained from the same, or another, site. A cartilage cap can include bio compatible gel, collagen and/or fresh cartilage. Fresh cartilage can include approximately 70% live chondrocytes.

Figure 2:
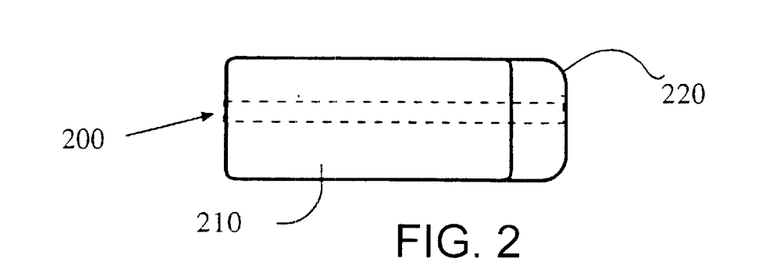
FIG. 2 illustrates a schematic side view of an osteochondral plug, representing an embodiment of the invention.

Referring to FIG. 2, an implantable prosthesis 200 is depicted. The implantable prosthesis 200 includes a porous substrate 210. The implantable prosthesis 200 includes a cap 220. The porous substrate 210 is coupled to the cap 220.

Figure 3:
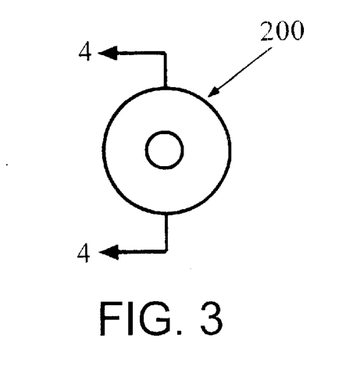
FIG. 3 illustrates a schematic end view of the osteochondral plug shown in FIG. 2.

Referring to FIG. 3, an end view of the implantable prosthesis 200 is shown. The section lines in FIG. 3 provide visual orientation for the view of the implantable prosthesis 200 shown in FIG. 4.

Figure 4:
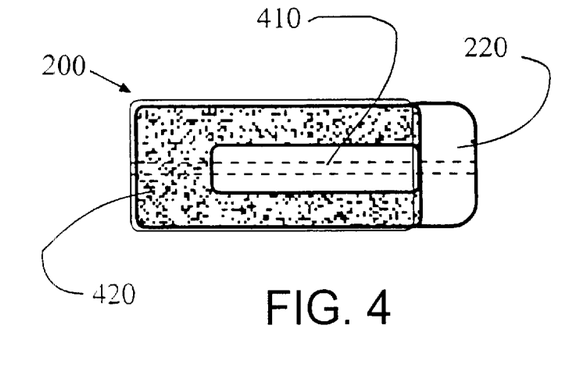
FIG. 4 illustrates a schematic sectional side view of the osteochondral plug shown in FIGS. 2 and 3.

Referring to FIG. 4, it can be appreciated that a cavity 410 is formed in the porous substrate 210. A pellet composed of elutable substance can be positioned within the cavity 410. The implantable prosthesis 200 also includes a shape memory metal sleeve 420. As discussed above, upon implantation, the shape memory material sleeve 420 can deflect, thereby producing stress to help hold the implantable prosthesis 200 in place. Of course, it is not necessary that both the pellet 100 and the porous substrate 210 both include shape memory materials. The invention can omit shape memory materials, include them in only one of the pellet 100 and the porous substrate 210, or include shape memory materials in both the pellet 100 and the porous substrate 210.

Surgical Context

A conventional arthroscopic set up includes an irrigating system, a viewing system and a positioning system in addition to the normal equipment utilized in a less invasive procedure conducted under general anesthesia.

The irrigating system involves a fluid (irrigant) source (typically two liter bags of normal or isotonic saline), connecting tubing to include tubing clamps for mechanically inhibiting and controlling the flow of the irrigating solution, the percutaneous catheter for insertion into the joint space to which the connecting tubing is attached providing the portal for irrigant supply, and a second portal or outflow port allowing irrigating fluid to exit the joint capsule which may have an extension tube to direct the outflow of the irrigant away from the operator.

Either (or both) of these catheters may be incorporated into a catheter system allowing the introduction of a "scope" (rod lens apparatus for viewing the interior of the joint space) or the introduction of all manner of interventional tools, to include probes cutters electrosurgical and electrothermal instruments. Some surgeons utilize a pump system that sense intra-articular pressure and maintains that pressure to insure distraction of the joint and adequate hemostasis. Otherwise, the intra-articular (joint capsule) pressure is generated by elevating the solution bags above the level of the patient making use of a simple gravity supply.

The viewing system includes the arthroscopic "scope" (optical rod lens) to which is typically attached a clip on video camera that feeds a video signal to the camera base and a CRT monitor for viewing.

A positioning system is selected, based upon the anatomy to be addressed with each procedure that is designed to immobilize or suspend the surgical site to facilitate the physician's access to the surgical field.

Instruments and Technique

The invention can utilize the above-described arthroscopic system for joint space access. The invention can include arthroscopic preparation of an appropriately sized recess into an osteochondral lesion of an articular joint surface and then subsequent arthroscopic delivery and implantation of a prosthesis carrying a chondrocyte inductive medicament.

The arthroscopic instruments can include a blunt trocar. The blunt trocar can be approximately 15 cm long with an internal diameter of approximately 4 mm.

Two alternative instrument approaches to preparing the sites and implanting the prostheses will now be described. The first approach is directed to separate exchangeable instruments for the recess preparation and prosthesis implantation steps. The second approach is directed to a combined instrument for effecting both the recess preparation and prosthesis implantation steps.

In the first instrument approach, the invention includes exchangeable catheter type devices. In this case, separate devices perform either the preparation function (e.g., drill the recess) or the delivery function (e.g., implant the prosthesis).

The exchangeable instruments for recess preparation can include a long cannula and a drill. The long catheter can be approximately 20 cm long with an internal diameter of approximately 3 mm. The long catheter is inserted into the blunt trocar and the drill is inserted into the long catheter. The drill needs to reach the subchondral bleeding bed. The drill can include a shaft of flexible wire coupled to a rigid tip. The flexible wire should extend beyond the proximal end of the long catheter. The drill can have a rigid tip of appropriate length (e.g., approximately 5 mm to approximately 15 mm) with a diameter of approximately 3 mm.

The exchangeable instruments for implantation can include a flexible catheter serially loaded with several, for example three, substrates. The flexible catheter is inserted into the blunt trocar. The flexible catheter can utilize a pressure flow mechanism to press-fit the plugs into the recesses that are located in the prepared bed.

Figure 5:
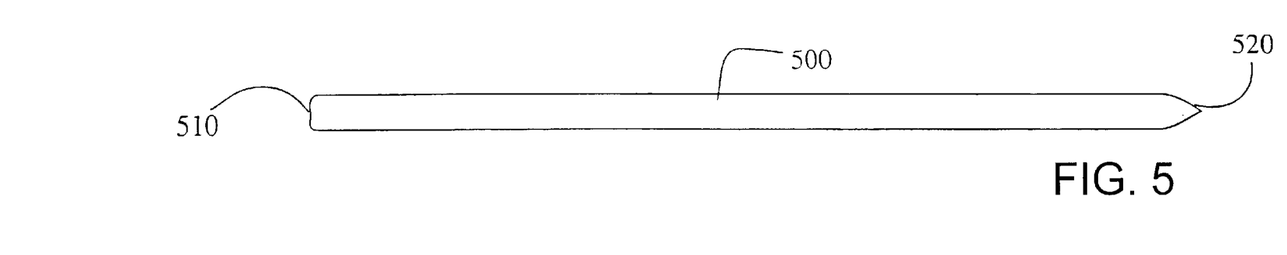
FIG. 5 illustrates a schematic side view of a blunt trocar for use in preparing sub-chondral recesses and implanting osteochondral plugs, representing an embodiment of the invention.

Referring to FIG. 5, a trocar 500 is depicted. The trocar 500 includes a proximal end 510 and a distal end 520.

Figure 6:
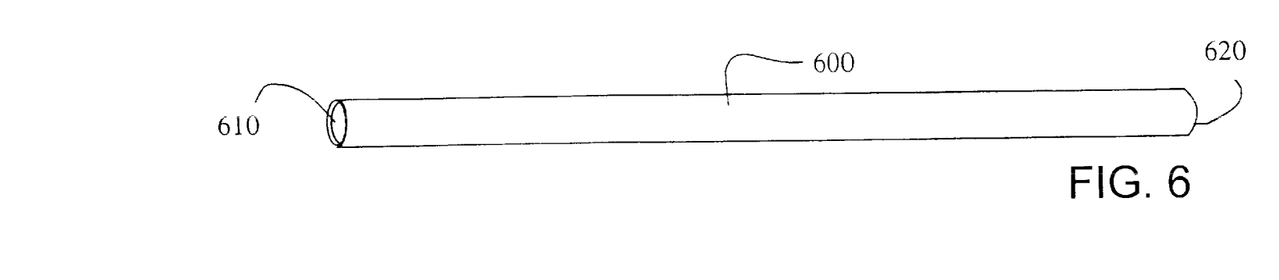
FIG. 6 illustrates a schematic side view of a long catheter for use in preparing subchondral recesses and implanting osteochondral plugs, representing an embodiment of the invention.

Referring to FIG. 6, a flexible catheter 600 is depicted. The flexible catheter 600 has a proximal end 610 and a distal end 620.

Figure 7:
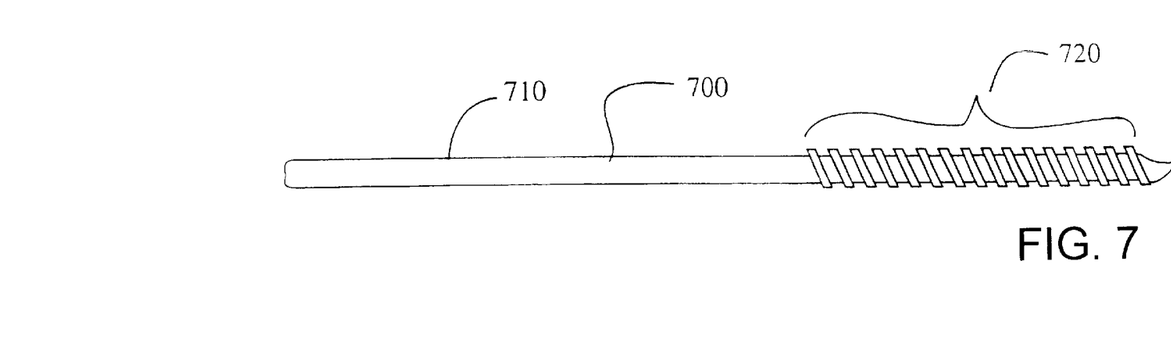
FIG. 7 illustrates a schematic side view of a stiff tip, flexible shaft twist drill for use in preparing sub-chondral recesses, representing an embodiment of the invention.

Referring to FIG. 7, a drill 700 is depicted. The drill 700 includes a flexible shaft 710. A rigid tip 720 is coupled to the flexible shaft 710.

Figure 8:
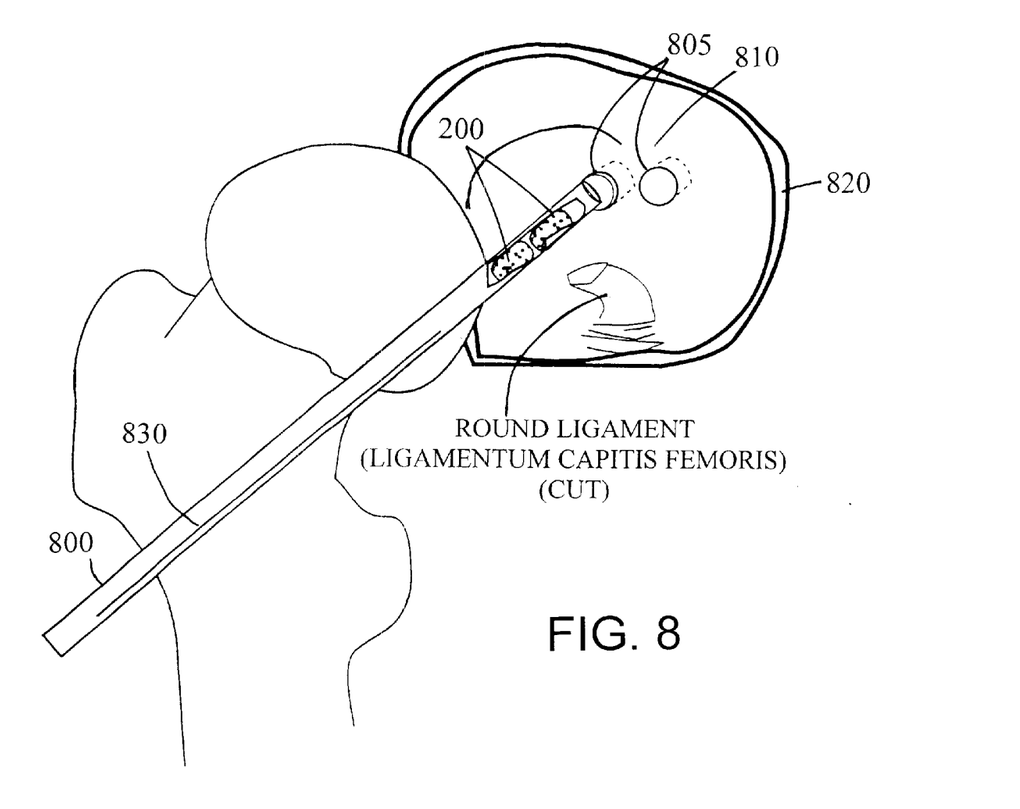
FIG. 8 illustrates a schematic isometric view of a surgical instrument assembly for use in implanting osteochondral plugs, representing an embodiment of the invention.

Referring to FIG. 8, a pellet inserter 800 is depicted inserting the implantable prosthesis 200 into a recess located within a prepared bed 810 of a bone 820. It can be appreciated from FIG. 8 that a plurality of recesses 805 have previously been prepared.

The pellet inserter 800 includes a plurality of serially arranged implantable prostheses 200 (e.g., 2 as shown in FIG. 8). By stacking the implantable prostheses 200 within the inserter 800, the physician can implant multiple prostheses without withdrawing the inserter 800 from the trocar (not shown in FIG. 8).

The pellet inserter 800 includes a force transmitting structure 830 to advance the prostheses 200 and force the prostheses 200 into the recesses 805. The structure 830 can be a spring, a flexible rod, a strut, a pneumatic subsystem and/or a hydraulic subsystem.

However, the use of exchangeable instruments requires the physician to alternately insert the two different instruments via the trocar and catheter as described above. This exchange of instruments requires time and effort. To save time, the physician can drill and plurality of recesses and then switch instruments to implant a corresponding plurality of plugs. This has the drawback of requiring the physician to realign the implantation instrument with each of the recesses previously produced by the first instrument. If the realignment is not done within tolerance, the plug may not be implanted properly.

In the second instrument approach, the invention can include a combined probe designed for both the preparation of recesses and the delivery of the medicament containing substrates into the recesses. Albeit mechanically more complex and bulky, the combined probe provides significant advantages. Specifically, less time is required because no exchange of instruments needs to take place. Further, no realignment is required because the combined probe can perform both functions at a site without being repositioned.

Figures 9, 10, 12:
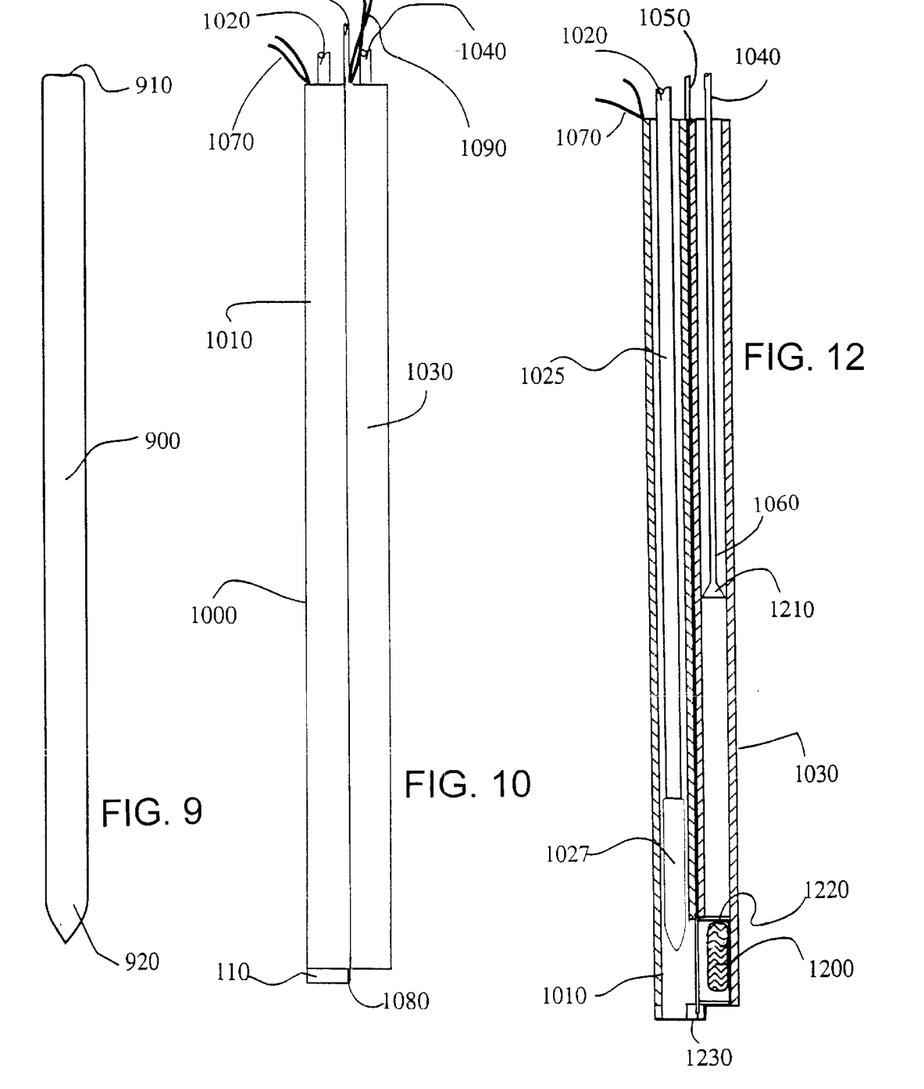
FIG. 9 illustrates a schematic side view of a large blunt trocar for use in preparing sub-chondral recesses, implanting osteochondral plugs and heat treating the resulting surfaces, representing an embodiment of the invention.
FIG. 10 illustrates a schematic side view of a surgical instrument for preparing sub-chondral recesses, implanting osteochondral plugs and heating treating the resulting surfaces, representing an embodiment of the invention.
FIG. 12 illustrates a schematic sectional side view of the surgical instrument shown in FIGS. 10 and 11.

Referring to FIG. 9, a trocar in 900 is depicted. The large trocar 900 includes a proximal end 910 and a distal end 920. The large trocar 900 is of greater internal diameter than the trocar shown in FIG. 5. This provides more room for working instruments at the expense of a slightly larger intrusion.

Referring to FIG. 10, a combined surgical instrument 1000 is depicted. The combined surgical instrument 1000 includes a hollow cylinder 1010 in which a drill 1020 is positioned. The combined surgical instrument 1000 also includes an implantable prosthesis magazine 1030 in which an advancement mechanism 1040 is located. The combined surgical instrument includes an actuator 1050 for transferring implantable prostheses from the magazine 1030 to the cylinder 1010.

The combined surgical instrument 1000 includes a heat source 1060 coupled to the advancement mechanism 1040. The heat source 1060 is powered by a pair of leads 1070. The combined surgical instrument 1000 includes a thermocouple 1080. The thermocouple 1080 is connected to a pair of leads 1090.

Figure 11:
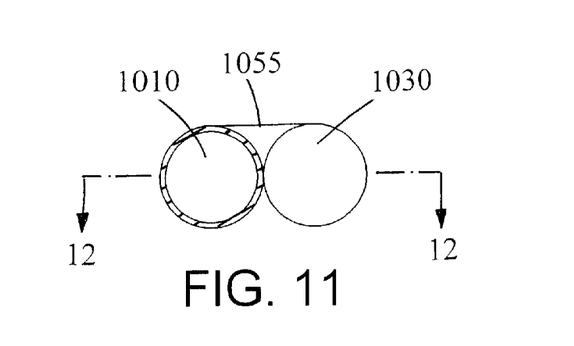
FIG. 11 illustrates a schematic end view of the surgical instrument shown in FIG. 10.
Figure 13:
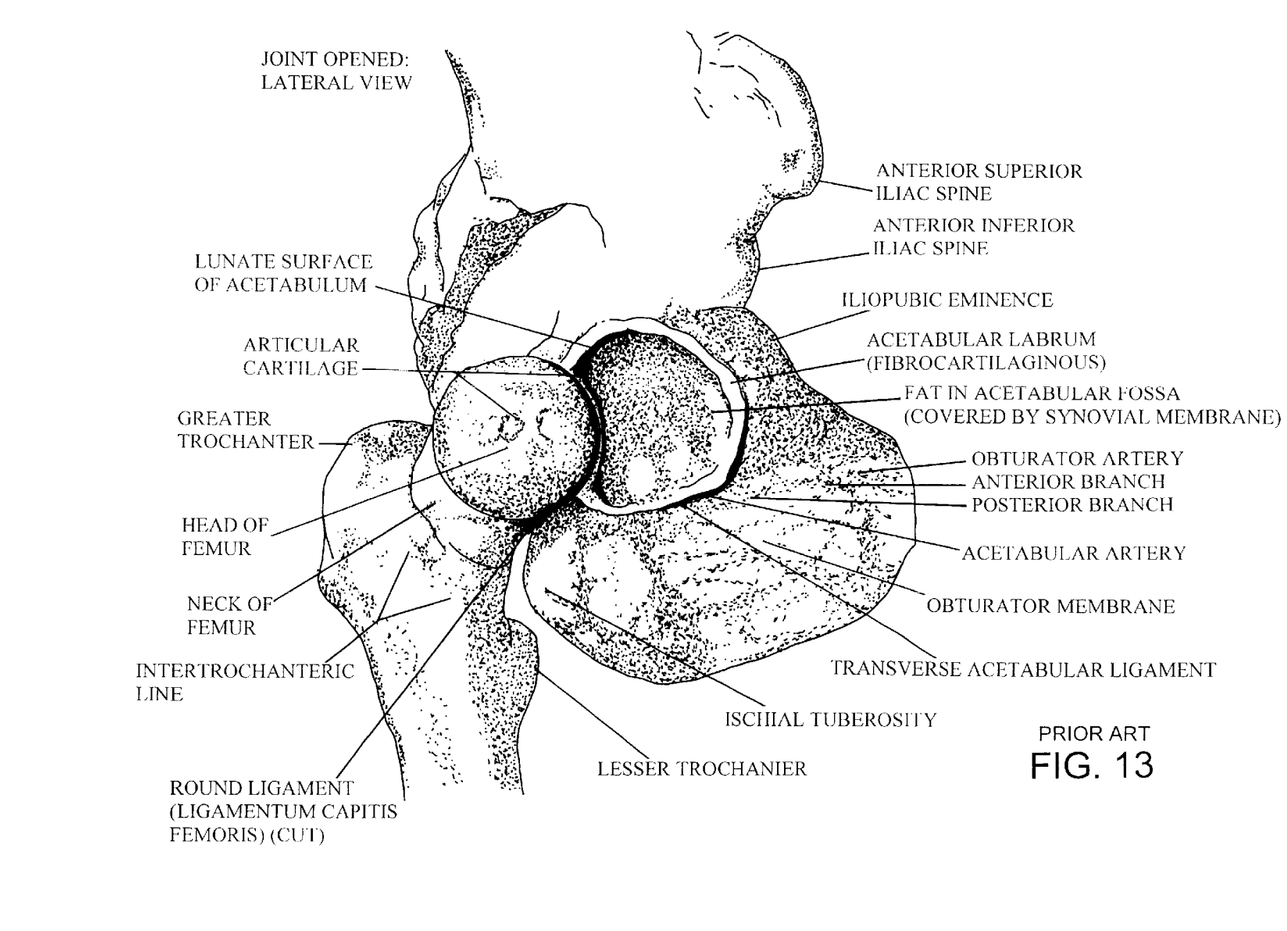
FIG. 13 illustrates a joint opened, lateral view of a human hip joint, appropriately labeled "prior art".

Referring to FIG. 11, an end view of the distal end of the combined surgical instrument 1000 is depicted. It can be appreciated from FIG. 11 that the cylinder 1010 is open at the distal end. It can also be appreciated from FIG. 11 that actuator 1050 is positioned within a channel 1055. The section lines in FIG. 11 provide visual reference for the cross-sectional image shown in FIG. 12.

Referring to FIG. 12, it can be appreciated that the drill 1020 includes a flexible shaft 1025 and a rigid tip 1027. As shown in FIG. 12, the tip 1027 has been withdrawn back away from the distal end so that an implantable prosthesis 1200 can be transferred from the magazine 1030 to the cylinder 1010. After transfer, the drill 1020 can be moved forward thereby pressing the rigid tip 1027 against the implantable prosthesis 1200 so as to force the implantable prosthesis 1200 out of the distal end of the combined surgical instrument 1000. After the implantable prosthesis 1200 has been inserted into the corresponding recess (not shown in FIG. 12), the drill 1020 can be withdrawn again and the transfer process repeated. Thus, the combined surgical instrument provides a significant advantage to the physician and patient in that a series of recesses can be prepared without having to either interchange instruments or move the distal end of the combined instrument from one recess site to another during the implantation step.

Still referring to FIG. 12, the advancement mechanism 1040 includes a piston 1210. The combined surgical instrument 1000 depicted in FIG. 12 contains only one implantable prosthesis 1200, the piston 1210 is depicted in a withdrawn position so that up to three additional implantable prostheses could be positioned within the magazine 1030. Of course, the length of the magazine can be increased to accommodate a large number of implantable prostheses.

The combined surgical instrument 1000 includes a pivoting carrier 1220. The pivoting carrier 1220 is rotationally fixed at the distal end of the combined surgical instrument 1000 with a bearing 1230. The actuator 1050 is coupled to the pivoting carrier 1220.

By making the diameter of the implantable prostheses smaller, the bulkiness of such a combined surgical instrument can be reduced. However, if the diameter of the implantable prostheses are too small, clinical problems may be encountered. Therefore, there is a trade off between the speed and alignment advantages provided by the combined surgical instrument versus its bulkiness.

The invention can also be included in a kit. The kit can include some, or all, of the components that compose the invention. More specifically, the kit can include the implants, the instruments and other components of the invention. The kit can also contain instructions for practicing the invention and apparatus for carrying out the invention. Unless otherwise specified, the components (and apparatus and/or instructions) of the kit can be the same as those used in the invention.

The term approximately, as used herein, is defined as at least close to a given value (e.g., preferably within 10% of, more preferably within 1% of, and most preferably within 0.1% of). The term substantially, as used herein, is defined as at least approaching a given state (e.g., preferably within 10% of, more preferably within 1% of, and most preferably within 0.1% of). The term coupled, as used herein, is defined as connected, although not necessarily directly, and not necessarily mechanically.

While not being limited to any particular performance indicator or diagnostic identifier, preferred embodiments of the invention can be identified one at a time by testing for improved growth of chondrocytes. The test for improved growth of chondrocytes can be carried out without undue experimentation by the use of a simple in vivo experiment. In this way, preferred compositions and/or configurations of substrates, pellets and/or caps can be identified one at a time.

EXAMPLE

A specific embodiment of the invention will now be further described by the following, nonlimiting example which will serve to illustrate in some detail various features of significance. The example is intended merely to facilitate an understanding of ways in which the invention may be practiced and to further enable those of skill in the art to practice the invention. Accordingly, the example should not be construed as limiting the scope of the invention.

A series of recesses are drilled in an area of chondral defects using the surgical devices shown in FIGS. 5–7. The recesses are drilled to a depth of approximately 10 mm (i.e., to the bleeding bed). A corresponding series of osteochondral plugs are inserted into the recesses using the surgical device shown in FIG. 8. The resulting surface area was treated (post implantation) with a TAC-S thermal probe at a temperature of 55° C. and a power of 23 Watts. Post-operative physical rehabilitation for 4 hours each day is begun immediately.

Practical Applications of the Invention

A practical application of the invention that has value within the technological arts is the treatment of osteochondral pathologies. For example, the invention can be used to treat chondromalacia and/or osteoarthritis, or the like. There are virtually innumerable uses for the invention, all of which need not be detailed here.

Advantages of the Invention

An implant, representing an embodiment of the invention, can be cost effective and advantageous for at least the following reasons. The invention provides a baited route to attract mesenchymal stem cells from the cancellous bone underlying the articular surfaces to chondral lesions within the joint, thereby promoting the growth of chondrocytes in the area of the chondral lesions.

All the disclosed embodiments of the invention described herein can be realized and practiced without undue experimentation. Although the best mode of carrying out the invention contemplated by the inventors is disclosed above, practice of the invention is not limited thereto. Accordingly, it will be appreciated by those skilled in the art that the invention may be practiced otherwise than as specifically described herein.

For example, the individual components need not be formed in the disclosed shapes, or assembled in the disclosed configuration, but could be provided in virtually any shape, and assembled in virtually any configuration. Further, the individual components need not be fabricated from the disclosed materials, but could be fabricated from virtually any suitable materials. Further, although the implant described herein can be a physically separate module, it will be manifest that the implant may be integrated into an apparatus with which it is associated. Furthermore, all the disclosed elements and features of each disclosed embodiment can be combined with, or substituted for, the disclosed elements and features of every other disclosed embodiment except where such elements or features are mutually exclusive.

It will be manifest that various additions, modifications and rearrangements of the features of the invention may be made without deviating from the spirit and scope of the underlying inventive concept. It is intended that the scope of the invention as defined by the appended claims and their equivalents cover all such additions, modifications, and rearrangements.

The appended claims are not to be interpreted as including means-plus-function limitations, unless such a limitation is explicitly recited in a given claim using the phrase "means for." Expedient embodiments of the invention are differentiated by the appended subclaims.

What is claimed is:

1. A surgical instrument, comprising:
   a trocar defining a lumen extending to a lumen opening at a distal end of the trocar, the trocar further comprising a magazine adjacent the trocar lumen for housing one or more implantable prostheses and a mechanism that transfers an implantable prosthesis to the trocar lumen;
   a drill positioned within the trocar lumen, the drill having a distal drill tip for preparing a subchondral bleeding bed for insertion of an implantable prosthesis, the drill tip being extendable distal relative to the lumen opening of the trocar and retractable proximal relative to where the transfer mechanism transfers the implantable prosthesis to the trocar lumen; and
   an advancement mechanism capable of causing an implantable prosthesis to be transferred into the trocar lumen when the drill tip is retracted.

2. The surgical instrument of claim 1, wherein the drill tip of the drill is attached to a proximal flexible shaft within the trocar lumen.

3. The surgical instrument of claim 1, further comprising a heat source coupled to the advancement mechanism.

4. The surgical instrument of claim 3, further comprising a thermocouple coupled to said heat source.

5. The surgical instrument of claim 3, wherein the transfer mechanism is a pivoting carrier adjacent a distal end of the trocar.

* * * * *